United States Patent [19]

Prill

[11] 4,140,513

[45] Feb. 20, 1979

[54] SODIUM SESQUIGLYPHOSATE

[75] Inventor: Erhard J. Prill, Kirkwood, Mo.

[73] Assignee: Monsanto Company, St. Louis, Mo.

[21] Appl. No.: 866,677

[22] Filed: Jan. 3, 1978

[51] Int. Cl.² ............................ A01N 9/36; C07F 9/38
[52] U.S. Cl. ............................................ 71/86; 71/76; 260/502.5
[58] Field of Search .................... 71/86, 76; 260/502.5

[56] References Cited

U.S. PATENT DOCUMENTS

| 3,799,758 | 3/1974 | Franz | 71/86 |
| 3,853,530 | 12/1974 | Franz | 71/86 |

*Primary Examiner*—Catherine L. Mills
*Attorney, Agent, or Firm*—Arnold H. Cole; Donald W. Peterson

[57] ABSTRACT

The sesquisodium salt of N-phosphonomethylglycine is a unique crystalline compound which has utility as a post-emergent herbicide and is also useful to increase the sucrose content of sugarcane.

16 Claims, No Drawings

SODIUM SESQUIGLYPHOSATE

N-phosphonomethylglycine, hereinafter referred to by its recognized common name, glyphosate, has the formula

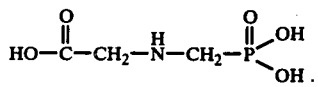

Since the compound is believed to exist as a zwitterion in the solid state, it could also be represented as

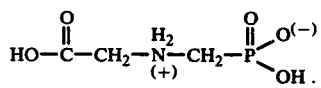

Glyphosate, and its use as a herbicide, is described in U.S. Pat. No. 3,799,758, while use as a plant growth regulator, including the treatment of sugarcane, is described in U.S. Pat. No. 3,853,530. Each of the patents includes within its disclosure, inter alia, the alkali metal salts of glyphosate, and the mono-, di- and trisodium salts are specifically identified.

It has now been found that the sesquisodium salt of glyphosate is a novel and unique compound which possesses the agricultural utilities mentioned above. In addition, sodium sesquiglyphosate has been found to possess other distinct and desirable properties which are not suggested by the prior art, nor are such properties present in the named sodium salts in said patents.

The sesquisodium salt of glyphosate is prepared by the partial neutralization of the acid with an appropriate base. The salt has, of course, a substantially 1.5 to 1 mole ratio of sodium cation to glyphosate anion. Useful bases for the neutralization include sodium carbonate, sodium bicarbonate, sodium hydroxide, sodium sulfite, sodium bisulfite, sodium sulfide, sodium formate, sodium acetate, sodium silicate and the like. As should be apparent, the donor source for the sodium cation can be chosen from a wide range of bases of both organic and inorganic acids. The use of sodium hydroxide is particularly preferred because of its ready availability, and also because of the ease with which the desired sesqui salt product is recovered following neutralization.

As noted at column 13, lines 5-8 of U.S. Pat. No. 3,799,758, the alkali metal salts of glyphosate are highly water-soluble. This is a desirable property in agriculturally useful active ingredients since such ingredients are often produced and marketed in liquid formulations, and the most economical and convenient diluent is water. Such high water-solubility typifies the mono-, di- and trisodium salts named in the prior art.

In many other instances, agriculturally useful active ingredients are produced and marketed in solid formulations. This permits application of the formulation as a powder or dust on the one hand, or, on the other hand, the desired amount of a liquid diluent can be added to a solid concentrate formulation at the application site prior to use. One significant advantage of such dry formulations is the reduction in container size and shipping weight.

Because of their high water-solubility, the mono-, di- and trisodium salts of glyphosate are not readily obtainable in a dry crystalline form. A glassy non-crystalline solid can be obtained by vacuum dehydration of a concentrated aqueous salt solution, but such solids are extremely hygroscopic and rapidly form a wet cake when exposed to air. Low temperature crystallization at about 0° C. or below can be employed to give these salts in crystalline form. However, as illustrated below, this process requires at least several days, and it is thus considered to be uneconomically slow.

It has now been found that this problem is not encountered with sodium sesquiglyphosate which, although also water soluble, crystallizes readily from concentrated aqueous solutions. For example, 33.86 grams of 99.6% glyphosate was neutralized at 25° C. with 12.3 grams of 98% sodium hydroxide in 21.5 grams of water. An extremely viscous slurry of crystals was obtained and spread on a glass plate to dry. The crystalline sesqui salt product thereafter lost water on oven drying indicating the presence of waters of hydration, and it was determined that prior to drying, the product was in the tetrahydrate form. The hydrated product decomposed at about 235° C., while the anhydrous product has an m.p. of > 300° C.

A number of additional neutralizations were carried out using more or less than 1.5 moles of the sodium cation per mole of glyphosate anion. In some of these runs the glyphosate was 99.6%, while a 95.3% glyphosate was used in other runs. In each run the crystalline product was collected and dried to a constant weight at 70° C. It was then titrated with standardized sodium hydroxide to determine the composition of the salt product (sesqui + mono or sesqui + di depending on whether the reactant ratio was more or less than the stoichiometric 1.5 : 1).

All of the runs were carried out using 0.1 mole of glyphosate, and the sodium hydroxide was employed as about a 30% solution in runs 1 – 10 (7.92 meq./gm.) or as about a 45% solution in runs 11 – 14 (10.87 meq./gm.). The total weight of all reactants in water was kept constant at 39.2 grams. The yields were calculated for the product which crystallized out of a 60% concentration reaction mixture and was oven-dried at 70° C. The results of these runs are tabulated below.

| | Sodium Sesquiglyphosate Preparations | | | | | |
|---|---|---|---|---|---|---|
| | Mole Ratio | | Glyphosate Assay, % | Yield % | Composition % | | |
| Run | Glyphosate | NaOH | | | Mono | Sesqui | Di |
| 1 | 2.00 | 2.90 | 99.6 | 42.4 | 0.4 | 99.6 | 0 |
| 2 | 2.00 | 2.95 | 99.6 | 57.3 | 0.2 | 99.8 | 0 |
| 3 | 2.00 | 3.00 | 99.6 | 47.7 | 0 | 100.0 | 0 |
| 4 | 2.00 | 3.05 | 99.6 | 51.1 | 0 | 99.8 | 0.2 |
| 5 | 2.00 | 3.10 | 99.6 | 50.8 | 0 | 98.7 | 1.3 |
| 6 | 2.00 | 2.85 | 95.3 | 53.1 | 0.3 | 99.7 | 0 |
| 7 | 2.00 | 2.90 | 95.3 | 65.8 | 0.5 | 99.5 | 0 |
| 8 | 2.00 | 2.95 | 95.3 | 57.9 | 0.3 | 99.7 | 0 |
| 9 | 2.00 | 3.00 | 95.3 | 68.8 | 0.3 | 99.7 | 0 |
| 10 | 2.00 | 3.05 | 95.3 | 54.0 | 0.1 | 99.9 | 0 |
| 11 | 2.00 | 2.50 | 99.6 | 19.2 | 3.25 | 96.75 | 0 |
| 12 | 2.00 | 2.75 | 99.6 | 37.2 | 0.5 | 99.5 | 0 |
| 13 | 2.00 | 3.25 | 99.6 | 45.3 | 0 | 94.55 | 5.45 |
| 14 | 2.00 | 3.50 | 99.6 | 21.7 | 0 | 27.4 | 72.6 |

From this data it will be seen that significant percentages of sodium sesquiglyphosate are obtained employing from about 1.25 to about 1.75 moles of the sodium cation per mole of glyphosate. As might be expected, the mixtures with the mono or di salts obtained at the outer limits of this range present some difficulties in separation, and it is preferred to employ a range of about 1.45 to 1.55 moles of sodium cation per mole of glyphosate. This more limited range serves to maximize yields of the sesqui salt and to simplify product recovery.

The examples which follow will illustrate the preparation of sodium sesquiglyphosate by acid neutralization with the sodium cation being introduced through a variety of sources.

Example 1

A 16.93 grams portion (0.1 mole) of 99.6% glyphosate was slowly added, with cooling to a solution of 7.95 grams (0.075 mole) of anhydrous sodium carbonate in 18.73 grams of water. The rate of addition was dictated by the vigorousness of the carbon dioxide evolution. After complete addition, the reaction mixture was heated to 70° C. to drive off the remaining carbon dioxide. The reaction mixture was then cooled first to room temperature, and thereafter in an ice bath to obtain maximum crystallization. The crystalline mass was broken up, and it was then isolated by filtration and air drying to give 9.99 grams of product. Said product was further dried overnight at 70° C. which produced a weight loss of 1.34 grams. This loss represents 98% of theory for the tetrahydrate, the small remainder of the water of hydration having been removed by the air drying. Titration of the anhydrous product with standardized sodium hydroxide showed 99.63% of sodium sesquiglyphosate and 0.37% of the monosodium salt.

Example 2

A 16.93 grams portion (0.1 mole) of 99.6% glyphosate was added to a solution of 9.5 grams (0.075 mole) of anhydrous sodium sulfite in 17.58 grams of water. The reaction mixture was heated to boiling to drive off most of the sulfur dioxide. The removal of sulfur dioxide was completed by evaporating two 100 ml. portions of distilled water from the reaction mixture on a steam bath, and then completing the evaporation to an essentially dry residue. The latter was dried overnight at 70° C. to give 20.65 grams of crystalline product. Titration with standardized sodium hydroxide showed 99.51% of sodium sesquiglyphosate and 0.49% of the monosodium salt.

Example 3

A 16.93 grams portion (0.1 mole) of 99.6% glyphosate was added to a solution of 18.0 grams (0.075 mole) of sodium sulfide nonahydrate in 50 grams of water. The addition was carried out slowly to moderate foaming due to rapid evolution of hydrogen sulfide. After the addition was completed, the reaction mixture was transferred to an evaporation dish, and two 100 ml. additions of distilled water were removed on a steam bath. The nearly dry product was then crushed with a spatula and air dried in a constant temperature/humidity chamber (23° C./50% relative humidity) to give 23.68 grams of product in a hydrated form. Overnight drying of the product at 70° C. gave 20.15 grams, and the weight loss is equivalent to 97.9% of theory for the tetrahydrate. Titration with standardized sodium hydroxide showed 99.74% of sodium sesquiglyphosate and 0.26% of the disodium salt.

Example 4

A 16.93 grams portion (0.1 mole) of 99.6% glyphosate was added to a solution of anhydrous sodium acetate (0.15 mole) in 19.08 grams of water. The reaction mixture was heated to the boiling point, and a strong odor of acetic acid was noted. Said mixture was then transferred to an evaporating dish, and three 100 ml. additions of distilled water were removed on a steam bath with further removal of acetic acid. Water removal was continued to give a nearly dry residue which was broken up and dried overnight to remove the water of hydration, leaving 20.55 grams of anhydrous product. Titration with standardized sodium hydroxide showed 99.35% of sodium sesquiglyphosate and 0.65% of the disodium salt.

Example 5

A 16.93 grams portion (0.1 mole) of 99.6% glyphosate was added slowly to a solution of 24.0 grams of sodium silicate (0.15 mole equivalents of sodium cation) in 150 ml. of water. The partially gelled solution was heated in an evaporating dish on a steam bath to remove water, leaving a granular residue of 30.52 grams. This residue was extracted three times with 200 ml. of hot water. The water extracts were evaporated to near dryness on a steam bath, and then heated overnight at 70° C. to give 20.86% grams of anhydrous product. Titration with standardized sodium hydroxide showed 99.88% of sodium sesquiglyphosate and 0.12% of the monosodium salt.

In order to demonstrate that the sodium sesquiglyphosate of this invention is physically distinct and different from the monosodium and disodium salts, crystals of each salt were prepared and subjected to an x-ray crystallographic study. The crystals of the sesqui salt were usually obtained as fine needles or prisms, and larger crystals were desired. In one attempt to meet this need, a solution of the sesqui salt was permitted to evaporate slowly in a petri dish covered with filter paper. A mass of fine crystals was obtained with a few larger crystals sticking out of the mass. In another approach, a somewhat less than saturated solution of the sesqui salt was permitted to stand in a flask covered with filter paper. Water was slowly lost after several days, and some larger crystals were formed. These larger crystals, along with those in the petri dish, were provided for the x-ray study.

To prepare mono salt crystals, a solution of 4.10 grams of 98% sodium hydroxide in 19.0 grams of water was maintained at 25°–30° C. with ice-bath cooling while 16.93 grams of 99.6% glyphosate was slowly added. The resulting 50% salt solution deposited 10.3 grams (air-dried) of cubic crystals after several days in a freezer at −7° C. No weight loss was noted during 4 hours at 70° C. The crystals were relatively large (3 mm. or over) and decomposed at 185° C. in a sealed tube when put into a hot bath. These crystals were provided for the x-ray study.

To prepare di salt crystals, a solution of 8.20 grams of 98% sodium hydroxide in 14.4 grams of water had 16.93 grams of 99.6% glyphosate slowly added. The 60% salt solution was placed in a freezer at −7° C. and seeded after several hours. The crystalline material used as seed was obtained by long standing of a few drops of disodium salt solution previously prepared. About a week after seeding, the solution became a solid mass of crystals. A 3.5 grams portion of this mass was slurried with 1.5 grams of water and filtered, after which the crystals were washed with ice water. The crystals were then placed in a 70° C. oven whereupon they turned into a dried, fused mass. The remainder of the first crystalline mass was slurried with 15.5 grams of water, filtered and washed with ice water. The resulting crystals were dried on a Buchner funnel to give glass-like prisms, m.p.

43°–45° C. These crystals lost water overnight and became chalky in appearance. The preparation was then repeated, and the ice water washed crystals were bottled wet and provided for the x-ray study.

The crystal data obtained in the study is summarized in the table below, the figures in parentheses being the estimated standard deviation in the least significant figures.

|  | 1.0 Na | 2.0 Na | 1.5 Na |
|---|---|---|---|
| a, Å | 7.126 (1) | 6.732 (1) | 11.09 (1) |
| b, Å | 11.216 (2) | 7.185 (1) | 5.483 (1) |
| c, Å | 9.680 (1) | 17.808 (3) | 15.031 (4) |
| α, deg. | 90.00 | 90.00 | 90.00 |
| β, deg. | 98.57 (1) | 94.06 (1) | 97.87 (2) |
| γ, deg. | 90.00 | 90.00 | 90.00 |
| V, Å³ | 765.0 (2) | 813.2 (2) | 905.5 (3) |
| Z | 4 | 2 | 4 |
| Space group | P2$_{1/c}$ | P2$_1$ | P2/N |

It was determined that the unit cell for the mono salt contains 4 glyphosate molecules, 4 sodium cations and 4 water molecules, said mono salt being in the monohydrate form. The unit cell for the di salt contains 2 glyphosate molecules, 4 sodium cations and 18 water molecules, said di salt being in the nonahydrate form. The unit cell for the sesqui salt contains 4 glyphosate molecules, 6 sodium cations and 8 water molecules, said sesqui salt being in the tetrahydrate form.

The results of the x-ray crystallographic structure determination clearly show that the sesqui salt compound is unique and not a physical mixture of the monosodium and the disodium salts. Taking the zwitterion representation for glyphosate, given above, the monosodium salt corresponds to the loss of the carboxylate hydrogen atom, while the disodium salt corresponds to the additional loss of the hydrogen bonded to the phosphate oxygen atom. The sesqui salt corresponds to a pair of glyphosate molecules (with 3 sodium cations), the carboxylate hydrogen being lost from each glyphosate molecule, and the phosphate hydrogen being lost from one of the glyphosate molecules. A graphic representation of a molecule of the sesqui salt might be shown as follows:

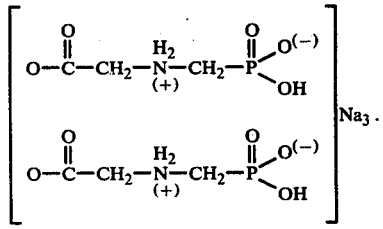

Example A

In determining the regulatory effects of the sesqui salt of this invention on sugarcane, it should be noted that the appropriate rate of application can vary from about 0.122 kg/hectare to about 5.6 kg/hectare. Depending upon local cultural practices in various areas around the world, sugarcane is grown for from about 9 to about 30 months before harvest, and it is thus necessary to consider both the chronological age and the maturity stage of the cane in rate determinations. Application of the treatment to the case is generally made from about 2 to 12 weeks prior to the scheduled harvest date. Preferably, such applications are made from 3 to 10 weeks before said date.

In this test individual sugarcane stalks are treated with compounds of this invention about 4–5 weeks before harvest. To avoid sampling errors, older cane, preferably 13 to 23 months old, is employed in the tests. For each compound employed, at least 5 stalks are used, processed and the total values obtained are averaged for each stalk. An identical number of untreated sugarcane stalks of the same age are similarly processed to provide a control. A comparison of the values obtained for the treated cane with the control sample provides a convenient means of determining the regulatory effectiveness of these compounds.

The analyses are carried out by the press method developed by T. Tanimoto and reported in Hawaiian Planters' Record, Volume 57, pp. 133–150 (1964). The data are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugarcane juice.

In order to convert a change in Pol percent Cane into a corresponding change in the quantity of sugar obtained, it is first necessary to know the average normal yield of sugar in the area under test. Here, the tests are carried out in a region where about 225 to 245 metric tons of cane are harvested per hectare, and about 22.5 metric tons of sugar are obtained from this quantity of cane. With this average normal yield of 22.5 metric tons per hectare, an increase of just 0.1 Pol percent Cane translates to an increase of about 225 kg of sugar per hectare.

About 38 mg. of the sesqui salt (on an acid equivalent basis) is dissolved in about 0.3 ml. of water. To this solution there is added a small amount (about 0.1% of the final volume) of a commercial nonionic surfactant (nonylphenol ethoxylated to contain about 9.5 mols of ethylene oxide per mol of nonylphenol). Such a solution is then applied to the whorl of each of the stalks to be tested with the exception of the control stalks. At the time of application, internode number 13 on each stalk is marked as a reference point. At 4 or 5 weeks after treatment (WAT), the plants are harvested, and the portion from the reference point to the shoot apex of each stalk of a treated or untreated group is removed, combined and analyzed as described. The results obtained are as follows:

|  | 4 WAT | | 5 WAT | |
|---|---|---|---|---|
|  | Juice Purity | Pol % Cane | Juice Purity | Pol % Cane |
| Treated | 76.97 | 9.25 | 78.23 | 9.54 |
| Untreated | 65.78 | 5.73 | 65.88 | 6.79 |

EXAMPLE B

In the sme geographical area, tests are also conducted on small field plots of sugarcane, applications being made by manual sprayers. The formulation contains about 74.5% of the sesqui salt of this invention, 2% of a commercial anionic surfactant (a complex of benzoic acid and sodium dioctyl sulfosuccinate), 9.5% of a dodecanethiol/urea complex and 14% of urea. The latter two ingredients serve to inhibit corrosion of metallic containers and spray equipment. The formulation is diluted with water for spraying, and it is applied to the sugarcane at each of the several rates (on an acid equivalent basis) noted below. The volume of water is about 185 liters/hectare, and parts of the treated and untreated plots are harvested at various time intervals and processed as described in Example I. The results obtained are as follows:

Application rate: 0.56 kg/hectare

|     | Untreated | | Treated | |
| --- | --- | --- | --- | --- |
| WAT | Juice Purity | Pol % Cane | Juice Purity | Pol % Cane |
| 4 | 70.55 | 7.55 | 84.39 | 12.36 |
| 5 | 74.93 | 8.37 | 85.07 | 11.87 |
| 6 | 75.33 | 9.50 | 81.96 | 11.54 |
| 7 | 75.16 | 8.11 | 83.96 | 12.68 |
| 8 | 78.39 | 9.06 | 85.57 | 12.86 |
| 9 | 75.58 | 8.41 | 87.52 | 13.67 |
| 10 | 70.60 | 7.05 | 86.03 | 13.50 |
| 12 | 68.06 | 6.68 | 85.01 | 12.18 |

Application rate: 0.84 kg/hectare

|     | Untreated | | Treated | |
| --- | --- | --- | --- | --- |
| WAT | Juice Purity | Pol % Cane | Juice Purity | Pol % Cane |
| 4 | 70.55 | 7.55 | 80.69 | 10.57 |
| 5 | 74.93 | 8.37 | 86.46 | 12.32 |
| 6 | 75.33 | 9.50 | 89.09 | 14.17 |
| 7 | 75.16 | 8.11 | 89.20 | 14.89 |
| 8 | 78.39 | 9.06 | 89.24 | 14.31 |
| 9 | 75.58 | 8.41 | 90.22 | 15.50 |
| 10 | 70.60 | 7.05 | 89.16 | 15.13 |
| 12 | 68.06 | 6.68 | 84.41 | 11.83 |

Application rate: 1.12 kg/hectare

|     | Untreated | | Treated | |
| --- | --- | --- | --- | --- |
| WAT | Juice Purity | Pol % Cane | Juice Purity | Pol % Cane |
| 4 | 70.55 | 7.55 | 84.84 | 11.83 |
| 5 | 74.93 | 8.37 | 86.31 | 13.10 |
| 6 | 75.33 | 9.50 | 88.19 | 14.14 |
| 7 | 75.16 | 8.11 | 88.99 | 14.72 |
| 8 | 78.39 | 9.06 | 88.60 | 14.53 |
| 9 | 75.58 | 8.41 | 91.66 | 16.39 |
| 10 | 70.60 | 7.05 | 89.84 | 14.81 |
| 12 | 68.06 | 6.68 | 88.86 | 14.42 |

Application rate: 2.24 kg/hectare

|     | Untreated | | Treated | |
| --- | --- | --- | --- | --- |
| WAT | Juice Purity | Pol % Cane | Juice Purity | Pol % Cane |
| 4 | 70.55 | 7.55 | 85.39 | 11.83 |
| 5 | 74.93 | 8.37 | 82.95 | 10.95 |
| 6 | 75.33 | 9.50 | 83.49 | 11.71 |
| 7 | 75.16 | 8.11 | 91.11 | 15.13 |
| 8 | 78.39 | 9.06 | 87.97 | 15.14 |
| 9 | 75.58 | 8.41 | 90.82 | 15.76 |
| 10 | 70.60 | 7.05 | 87.98 | 13.33 |
| 12 | 68.06 | 6.68 | 89.15 | 16.15 |

Application rate: 4.48 kg/hectare

|     | Untreated | | Treated | |
| --- | --- | --- | --- | --- |
| WAT | Juice Purity | Pol % Cane | Juice Purity | Pol % Cane |
| 4 | 70.55 | 7.55 | 76.71 | 8.62 |
| 5 | 74.93 | 8.37 | 81.88 | 10.15 |
| 6 | 75.33 | 9.50 | 82.11 | 10.53 |
| 7 | 75.16 | 8.11 | 80.88 | 10.23 |
| 8 | 78.39 | 9.06 | 78.08 | 9.19 |
| 9 | 75.58 | 8.41 | 77.82 | 8.74 |
| 10 | 70.60 | 7.05 | 76.38 | 8.36 |
| 12 | 68.06 | 6.68 | 79.46 | 9.84 |

Example C

In a different geographical area, small field plots of sugarcane which had been grown for about 14 months are treated with substantially the same formulation of the sesqui salt as employed in Example II. The volume of diluent water is about 300 liters/hectare, and application is by means of a $CO_2$ operated sprayer. Twenty stalks of cane are taken as a sample at each harvest date, and each stalk is trashed and topped at the point of attachment of the 5 to 6 leaf sheath. In the results from this test presented below, ERS represents the estimated recoverable sugar in tons per hectare.

|     | 2 WAT | | 5 WAT | | 8 WAT | | 12 WAT | |
| --- | --- | --- | --- | --- | --- | --- | --- | --- |
|     | JP | ERS | JP | ERS | JP | ERS | JP | ERS |
| Untreated | 81.8 | 8.78 | 80.4 | 10.14 | 83.7 | 13.21 | 87.3 | 15.55 |
| 0.22 (kg/ha) | 82.7 | 10.18 | 80.8 | 11.69 | 85.5 | 15.20 | 88.3 | 16.78 |
| 0.45 (kg/ha) | 82.1 | 10.32 | 81.2 | 12.17 | 87.0 | 16.25 | 88.4 | 17.09 |
| 0.67 (kg/ha) | 80.8 | 9.60 | 81.4 | 11.69 | 88.2 | 16.30 | 89.4 | 17.76 |
| 1.12 (kg/ha) | 81.9 | 9.83 | 80.4 | 11.63 | 87.4 | 15.34 | 88.3 | 15.94 |

JP = juice purity

Example D

In a third geographical area of the world, small field plots of sugarcane which had been grown for about 8 months are treated with substantially the same formulation of the sesqui salt as employed in Example II. Application is by means of a hand-held sprayer, and the volume of diluent water is about 385–390 liters/hectare. The samples at each harvest date consists of ten stalks, and the following data is obtained.

|     | 2 WAT | | 4 WAT | | 6 WAT | | 8 WAT | |
| --- | --- | --- | --- | --- | --- | --- | --- | --- |
|     | Juice Purity | Pol % Cane | Juice Purity | Pol % Cane | Juice Purity | Pol % Cane | Juice Purity | Pol % Cane |
| Untreated | 75.95 | 7.34 | 73.63 | 6.98 | 76.65 | 8.09 | 81.61 | 9.33 |
| 0.28 (kg/ha) | 75.59 | 7.08 | 74.25 | 6.85 | 76.38 | 8.27 | 83.02 | 9.78 |
| 0.56 (kg/ha) | 78.05 | 8.05 | 76.58 | 7.66 | 78.62 | 8.71 | 83.24 | 9.91 |
| 0.84 (kg/ha) | 75.50 | 7.58 | 76.29 | 7.59 | 78.24 | 8.58 | 83.16 | 10.01 |
| 1.12 (kg/ha) | 72.72 | 7.02 | 76.86 | 7.47 | 79.72 | 9.26 | 81.94 | 9.63 |

Example E

The post-emergence herbicidal activity of sodium sesquiglyphosate of this invention is demonstrated as follows. The active ingredient is applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given below, and the plant species treated are each represented by a code letter as follows:

| | |
|---|---|
| A - Canada Thistle | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Nutsedge | Q - Wild Buckwheat |
| H - Quackgrass | R - Hemp Sesbania |
| I - Johnsongrass | S - Panicum Spp |
| J - Downy Brome | T - Crabgrass |

The post-emergence herbicidal activity index used is as follows:

| Plant Response | Index |
|---|---|
| 0-24% Injury | 0 |
| 25-49% Injury | 1 |
| 50-74% Injury | 2 |
| 75-99% Injury | 3 |
| All Killed | 4 |

| | | Plant Species | | | | | | | | | |
|---|---|---|---|---|---|---|---|---|---|---|---|
| WAT | kg ha | A | B | C | D | E | F | G | H | I | J | K |
| 2 | 11.2 | 2 | 2 | 4 | 3 | 4 | 4 | 3 | 3 | 3 | 3 | 4 |
| 4 | 11.2 | 4 | 3 | 4 | 4 | 4 | 4 | 4 | 4 | 4 | 4 | 4 |
| 2 | 5.6 | 2 | 2 | 2 | 2 | 4 | 4 | 2 | 3 | 2 | 2 | 3 |
| 4 | 5.6 | 3 | 3 | 3 | 3 | 4 | 4 | 3 | 4 | 3 | 2 | 4 |

| | | Plant Species | | | | | | | | | | | | |
|---|---|---|---|---|---|---|---|---|---|---|---|---|---|---|
| WAT | kg ha | L | M | N | O | P | B | Q | D | R | E | F | C | J | S | K | T |
| 2 | 5.6 | 3 | 3 | 3 | 4 | 3 | — | 3 | 2 | 3 | 4 | 3 | 2 | 3 | 3 | 3 | 3 |
| 4 | 5.6 | 3 | 4 | 4 | 4 | 4 | — | 3 | 2 | 4 | 4 | 4 | 2 | 4 | 4 | 4 | 4 |
| 2 | 1.12 | 1 | 1 | 2 | 2 | 2 | 2 | 1 | 2 | 1 | 3 | 3 | 1 | 1 | 3 | 3 | 3 |
| 4 | 1.12 | 1 | 3 | 2 | 4 | 2 | 2 | 2 | 2 | 1 | 4 | 3 | 1 | 1 | 4 | 4 | 3 |
| 2 | 0.28 | 0 | 0 | 2 | 0 | 1 | 1 | 0 | 0 | 0 | 1 | 1 | 0 | 1 | 2 | 1 | 1 |
| 4 | 0.28 | 0 | 3 | 1 | 0 | 1 | 1 | 1 | 1 | 1 | 2 | 2 | 0 | 1 | 3 | 2 | 2 |

For herbicidal use, the appropriate rate of application can vary from about 0.28 kg/hectare to about 22.4 kg/hectare.

It will be understood that agriculturally useful compositions incorporating the active ingredient of this invention can be employed in either solid or liquid form. Such compositions are prepared by admixture of said active ingredient with an adjuvant such as a diluent, extender, carrier or conditioning agent to provide for application as a particulate solid, a solution or a dispersion. From the standpoint of economy and convenience, liquid compositions using water as a diluent are preferred.

The agriculturally useful compositions will preferably contain from about 0.5 to about 20.0 parts by weight of a surface-active agent in order to enhance wetting, dispersion, suspension, absorbtion and the like. Anionic, cationic, non-ionic and amphoteric types are all included within the class of surface-active agents which can be employed for such purposes.

Preferred wetting agents are alkyl benzene and alkyl naphthalene sulfonates, sulfated fatty alcohols, amines or acid amines, long chain acid esters of sodium isothionate, esters of sodium sulfosuccinate, sulfated or sulfonated fatty acid esters petroleum sulfonates, sulfonated vegetable oils, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N(long chain acid)taurates.

The inert carriers and extenders are preferably of mineral origin including natural clays, some pyrophyllites and vermiculite. Typical finely-divided solids which can be so used in compositions of this invention may be exemplified by diatomaceous earth, fuller's earth, kaolinites, attapulgite or montmorillionite clays, bentonites, synthetic silicas, calcium carbonate and calcium sulfate dihydrate. Such materials can be present in the compositions in amounts of from about 3 to about 95 parts by weight.

Agriculturally useful compositions of the active ingredient of this invention may also contain small amounts, up to at least 10% by weight of a variety of additives to enhance specific features. Among these additives are anti-caking or flow control agents, anti-corrosion agents, defoamers, perfumes and dyes.

While the invention has been described herein with regard to certain representative examples for purpose of illustrating its practice, it is not to be construed as limited thereto. Those skilled in the art will readily recognize the variations and modifications which can be made without departing from the spirit and scope of the invention.

What is claimed is:

1. Sodium salt of N-phosphonomethylglycine wherein the molar ratio of sodium cation to acid anion is substantially 1.5 to 1.

2. A salt as defined in claim 1 which is in the tetrahydrate form.

3. A composition for use as a herbicide or for use to increase the sucrose content of sugarcane comprising an effective amount of a sodium salt of N-phosphonomethylglycine wherein the molar ratio of sodium cation to acid anion is substantially 1.5 to 1, and at least one adjuvant.

4. A composition for increasing the sucrose content of sugarcane comprising an effective amount of a sodium salt of N-phosphonomethylglycine wherein the molar ratio of sodium cation to acid anion is substantially 1.5 to 1, and at least one adjuvant.

5. A herbicidal composition comprising an effective amount of a sodium salt of N-phosphonomethylglycine wherein the molar ratio of sodium cation of acid anion is substantially 1.5 to 1, and at least one adjuvant.

6. A composition as defined in claim 3 wherein said adjuvant comprises from about 0.5 to about 20.0 parts by weight of a surface-active agent.

7. A composition as defined in claim 3 wherein said adjuvant comprises from about 3 to about 95 parts by weight of an inert carrier or extender.

8. A composition as defined in claim 6 wherein said adjuvant comprises from about 3 to about 95 parts by weight of an inert carrier or extender.

9. A herbicidal method which comprises contacting a plant with a herbicidally effective amount of a sodium salt of N-phosphonomethylglycine wherein the molar ratio of sodium cation to acid anion is substantially 1.5 to 1.

10. A method as defined in claim 9 wherein said amount is from about 0.28 to about 22.4 kg/hectare.

11. A method for increasing the sucrose content of sugarcane which comprises applying to said sugarcane an effective amount of a sodium salt of N-phosphonomethylglycine wherein the molar ratio of sodium cation to acid anion is substantially 1.5 to 1.

12. A method as defined in claim 11 wherein said amount is from about 0.112 to about 5.6 kg/hectare.

13. A method as defined in claim 11 wherein said salt is applied to the sugarcane from about 2 to about 12 weeks prior to harvest.

14. A method as defined in claim 11 wherein said salt is applied to the sugarcane from about 3 to about 10 weeks prior to harvest.

15. A method as defined in claim 12 wherein said salt is applied to the sugarcane from about 2 to about 12 weeks prior to harvest.

16. A method as defined in claim 12 wherein said salt is applied to the sugarcane from about 3 to about 10 weeks prior to harvest.

* * * * *